(12) United States Patent
Shi et al.

(10) Patent No.: US 11,566,986 B2
(45) Date of Patent: Jan. 31, 2023

(54) ROCK DRILLING EXPERIMENTAL DEVICE AND METHOD FOR SIMULATING TRUE TRIAXIAL CONDITIONS OF DEEP WELL DRILLING

(71) Applicant: SOUTHWEST PETROLEUM UNIVERSITY, Chengdu (CN)

(72) Inventors: Xiangchao Shi, Chengdu (CN); Xinhao Yang, Chengdu (CN); Shuai Chen, Chengdu (CN); Yanzhou Chen, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 0 days.

(21) Appl. No.: 17/834,075

(22) Filed: Jun. 7, 2022

(65) Prior Publication Data
US 2022/0390339 A1 Dec. 8, 2022

(30) Foreign Application Priority Data
Jun. 7, 2021 (CN) .......................... 202110631410.6

(51) Int. Cl.
*G01N 3/00* (2006.01)
*G01N 3/10* (2006.01)
*G01N 33/24* (2006.01)

(52) U.S. Cl.
CPC .............. *G01N 3/10* (2013.01); *G01N 33/24* (2013.01); *G01N 2203/0019* (2013.01); *G01N 2203/0048* (2013.01); *G01N 2203/0256* (2013.01)

(58) Field of Classification Search
CPC .. G01N 3/10; G01N 33/24; G01N 2203/0019; G01N 2203/0048; G01N 2203/0256
See application file for complete search history.

(56) References Cited

U.S. PATENT DOCUMENTS

| | | | |
|---|---|---|---|
| 2017/0003263 A1* | 1/2017 | Huang | .................... G01N 33/24 |
| 2018/0284758 A1* | 10/2018 | Celia | ...................... H04L 1/0041 |

(Continued)

FOREIGN PATENT DOCUMENTS

| | | |
|---|---|---|
| CN | 102011582 A | 4/2011 |
| CN | 102221501 A | 10/2011 |

(Continued)

OTHER PUBLICATIONS

First Office Action issued in counterpart Chinese Patent Application No. 202110631410.6, dated Dec. 3, 2021.

*Primary Examiner* — Max H Noori
(74) *Attorney, Agent, or Firm* — Westbridge IP LLC

(57) ABSTRACT

Disclosed are a rock drilling experimental device and a method for simulating true triaxial conditions of deep well drilling; the device includes an energy supply module, an experimental loading module, a hydraulic supply module, a parameter control module and a data acquisition module. The device provides power through the energy supply module; the experimental loading module applies three directional stresses, a liquid column pressure and a pore pressure to a rock specimen by simulating a formation environment, and simultaneously drills into the rock specimen with a bit; the hydraulic supply module provides a hydraulic pressure to the liquid column pressure, the pore pressure and the three directional stresses in the experimental loading device; and the parameter control module is used to control a displacement module of the experimental loading module to move, and adjust a displacement, the pressure and a temperature to the target values.

8 Claims, 8 Drawing Sheets

(56) References Cited

U.S. PATENT DOCUMENTS

2020/0386659 A1\* 12/2020 Li ......................... E21B 49/003
2022/0253761 A1\* 8/2022 Jamieson ........... G06Q 10/0633

FOREIGN PATENT DOCUMENTS

| | | | | | |
|---|---|---|---|---|---|
| CN | 103806907 | A | | 5/2014 | |
| CN | 105863627 | A | | 8/2016 | |
| CN | 105938070 | A | | 9/2016 | |
| CN | 106018100 | A | | 10/2016 | |
| CN | 106323788 | A | | 1/2017 | |
| CN | 107505207 | A | | 12/2017 | |
| CN | 105510142 | B | \* | 2/2018 | ............... G01N 3/12 |
| CN | 107893652 | A | \* | 4/2018 | ............. E21B 43/26 |
| CN | 108952671 | A | | 12/2018 | |
| CN | 210264683 | U | | 4/2020 | |
| CN | 212614665 | U | | 2/2021 | |
| CN | 112525671 | A | | 3/2021 | |
| CN | 212658548 | U | | 3/2021 | |
| FR | 2937133 | A1 | | 4/2010 | |
| GB | 2201790 | A | | 9/1988 | |

\* cited by examiner

ROCK DRILLING EXPERIMENTAL DEVICE AND METHOD FOR SIMULATING TRUE TRIAXIAL CONDITIONS OF DEEP WELL DRILLING

CROSS-REFERENCE TO RELATED APPLICATIONS

This application claims priority to Chinese Patent Application No. 202110631410.6, filed on Jun. 7, 2021, the contents of which are hereby incorporated by reference.

TECHNICAL FIELD

The application relates to the technical field of speed-up in deep well drilling, and in particular to a rock drilling experimental device and a method for simulating true triaxial conditions of deep well drilling.

BACKGROUND

In oil and gas drilling engineering, how to break rocks efficiently and improve a drilling efficiency is an eternal theme. However, a real bottom hole environment of deep well drilling is complex, and an influence law of factors such as a high temperature, a high pressure, a high ground stress on a rock crushing efficiency of tools is unclear, thus seriously affecting an innovation of a speed-up technology in deep well drilling. In the existing rock drillability experimental evaluation methods and standards, rock drillability tests are usually carried out without simulating any bottom hole environment. Therefore, the tests are far from real bottom hole conditions of deep well drilling, and may not provide an effective support for an improvement of the speed-up technology in drilling.

In the application with a patent number of CN103806907B, a device and a method for testing rock drillability in deep and ultra-deep well drilling are put forward. This device realizes the rock drillability test under a conventional triaxial condition (two horizontal principal stresses are equal), but the device still may not represent the influence of unequal horizontal principal stresses on the rock drillability in complicated formations.

To sum up, at present, it is urgent to design a rock drilling experimental device and a method for simulating true triaxial conditions of deep well drilling, and then get the influence law of the high temperature, the high pressure and the high ground stress at the real bottom hole of deep well drilling on the rock crushing efficiency.

SUMMARY

The main objective of the application is to provide a rock drilling experimental device and a method for simulating true triaxial conditions of deep well drilling, which improve an accuracy of a drillability evaluation by simulating a true triaxial stress of a formation, and a liquid column pressure, a pore pressure and high temperature conditions of a bit drilling into a wellbore.

In order to achieve the above objective, the application provides the rock drilling experimental device and the method for simulating the true triaxial conditions of deep well drilling; the device includes an energy supply module, an experimental loading module, a hydraulic supply module, a parameter control module and a data acquisition module; the energy supply module, the experimental loading module and the hydraulic supply module are connected with each other through pipelines, and the parameter control module and the data acquisition module are connected with the experimental loading module through cables.

Optionally, the energy supply module includes a three-phase asynchronous motor, an oil cooler, a differential pressure transmitter and an L-shaped support frame; the three-phase asynchronous motor is arranged on a bottom plate of the L-shaped support frame; the oil cooler and the differential pressure transmitter are arranged on a side wall of the L-shaped support frame; the differential pressure transmitter is arranged above the oil cooler; the differential pressure transmitter, the oil cooler and the three-phase asynchronous motor are connected in sequence through the pipelines.

Optionally, the experimental loading module includes a column support structure, a sleeve lifting mechanism, a sleeve, a loading chamber, a support plate lifting mechanism, a support plate, a base and a drilling structure; the column support structure includes a plurality of smooth columns and threaded columns which are symmetrically arranged on both sides above the base; the sleeve is connected with the sleeve lifting mechanism; the support plate is connected with the support plate lifting mechanism; the sleeve lifting mechanism and the support plate lifting mechanism are connected with the threaded columns on both sides of the column support structure through threads; the sleeve lifting mechanism is arranged above the support plate lifting mechanism; the drilling structure includes a bit, a drill rod, a transmission chain and a servo motor; the bit is matched with the drill rod through a threaded connection, and is suitable for a study of a rock breaking mechanism of multiple bits, and the multiple bits, including PDC bits and cone bits, may be used; the threaded connection makes a replacement of the bit simple and convenient; the servo motor is fixedly installed on an inner wall surface of the base; one end of the drill rod is connected with the servo motor through the transmission chain, and the bit drills into a rock from bottom to top through the drill rod; detritus is separated from a rock mass by the gravity of broken detritus, and the detritus are discharged in time, so an influence of the detritus on an experimental process is reduced; the other end of the drill rod passes through a through hole at the bottom of the support plate lifting mechanism and is installed on a groove.

Optionally, a top center of the sleeve is provided with a pore pressure hole; a bottom end of the drill rod is provided with a liquid column pressure hole.

Optionally, the loading chamber includes a plurality of heating resistors, a cube rock specimen, a first X-direction loading plate, a second X-direction loading plate, a first Y-direction loading plate and a second Y-direction loading plate; and a tail part of each loading plate is uniformly distributed with two stress bars and a plurality of horizontal stress holes, and the double bars on each loading plate avoid an uneven stress and a stress concentration in a process of pressing.

Optionally, the top and the bottom of the loading chamber are provided with sealing rings.

Optionally, the loading chamber has a circular structure; there is a square vacant space in the middle of the loading chamber where the heating resistors are installed, the cube rock specimen is placed, the first X-direction loading plate, the second X-direction loading plate, the first Y-direction loading plate and the second Y-direction loading plate reciprocate; the heating resistors are uniformly distributed on four circumferential inner walls of the loading chamber; two horizontal stress holes are uniformly arranged on each surface of the four circumferential inner walls of the loading chamber; the first X-direction loading plate, the second X-direction loading plate, the first Y-direction loading plate and the second Y-direction loading plate are respectively connected with the loading chamber through the two horizontal stress holes on each surface, so that magnitudes of principal stresses in three directions of the rock specimen are independently changed, and shortcomings of conventional triaxial experiments are solved.

Optionally, the first X-direction loading plate, the second X-direction loading plate, the first Y-direction loading plate and the second Y-direction loading plate respectively face four directions; two adjacent loading plates are perpendicular to each other, and a contact part of the two vertical loading plates is in a staggered contact mode between an end face and a front face, so that the rock specimen is tightly pressed and a friction and a dislocation between the loading plates can be avoided at the same time; the first X-direction loading plate, the second X-direction loading plate, the first Y-direction loading plate and the second Y-direction loading plate enclose a structure with a vacant space in the center, and the vacant space is used for placing the cube rock specimen.

Optionally, the hydraulic supply module has four combinations of hydraulic pumps and oil tanks; the hydraulic pumps include a liquid column hydraulic pump, a pore hydraulic pump, an X-direction hydraulic pump and a Y-direction hydraulic pump; the oil tanks include a liquid column pressure tank, a pore pressure tank, an X-direction pressure tank and a Y-direction pressure tank; the hydraulic pumps and the oil tanks are all connected by flanges, and then fixed on the support plate.

Optionally, the parameter control module includes a plurality of controllers and sensors; the controllers include a rotation speed controller for controlling the bit to rotate at a specified rotation speed, a displacement controller for controlling the sleeve lifting mechanism, the support plate lifting mechanism and the loading plates to realize a displacement change, a pressure controller for controlling the pore pressure, the liquid column pressure, the loading plates and the sleeve lifting mechanism to realize a pressure change, and a temperature controller for controlling a temperature change of the heating resistors in the loading chamber; the sensors include an axial pressure sensor for detecting the pressure change of the sleeve lifting mechanism, a pore pressure sensor for detecting an axial pore pressure change, a first displacement sensor for detecting a moving distance of each loading plate, a first pressure sensor for detecting the pressure change of each loading plate, a temperature sensor for detecting the temperature change of each heating resistor, a second displacement sensor for detecting a relative moving distance of the bit and a second pressure sensor for detecting the pressure change of the bit.

A rock drilling experimental method for simulating true triaxial conditions of deep well drilling adopts the rock drilling experimental device for simulating the true triaxial conditions of deep well drilling, and includes the following steps:

Step 1, preparing the cube rock specimen, selecting an experimental bit, installing the bit on the drill rod in a threaded connection way, and starting a data acquisition device to collect real-time data;

Step 2, starting the energy supply module, providing an energy power for the rock drilling experimental device by using the three-phase asynchronous motor, cooling the three-phase asynchronous motor by using the oil cooler, and checking whether a differential pressure of the rock drilling experimental device is within a set value by using the differential pressure transmitter;

Step 3, placing the cube rock specimen in a square hole at the bottom of the loading chamber;

Step 4, starting the parameter control module, operating according to a sequence of a coarse adjustment by using the displacement controller and a precise adjustment by using the pressure controller, controlling the four loading plates to slowly move to the cube rock specimen until the four loading plates completely contact the cube rock specimen, and applying a load to the set value;

Step 5, slowly lowering the sleeve lifting mechanism by using the displacement controller, and operating according to the sequence of the coarse adjustment by using the displacement sensor and the precise adjustment by using the pressure sensor, ensuring that the bottom of the sleeve lifting mechanism is tightly attached to the cube rock specimen; and then turning on the heating resistors by using the temperature controller, preheating the loading plates and the cube rock specimen until the temperature sensor reaches a predetermined value, and keeping the predetermined value for a period of time;

Step 6, controlling the support plate lifting mechanism to move downwards by using the displacement controller, and in this process, providing a rotary force for the bit without starting the rotation speed controller; the same as an adjustment mode in Step 4, operating according to the sequence of the coarse adjustment by using the displacement sensor and the precise adjustment by using the pressure sensor until the top of the bit contacts the bottom of the cube rock specimen;

Step 7, starting the pressure controller to inject the hydraulic oil in the liquid column pressure tank into the liquid column pressure hole and the hydraulic oil in the pore pressure tank into the pore pressure hole, and then starting the rotation speed controller and the displacement controller to control the bit to drill according to the set value;

Step 8, collecting, outputting and saving the data of the time, the temperature, the pressure, the rotation speed and the drilling depth in the experimental process by using the data acquisition module, and finishing a data acquisition and processing of the experiment;

Step 9, firstly, turning off the rotation speed controller to stop the drilling of the bit, and then turning off the pressure controller and connecting a nitrogen bottle to the loading chamber through the pipelines; flowing the hydraulic oil from the pore pressure hole back to the pore pressure tank and from the liquid column pressure hole back to the liquid column pressure tank, and turning on the displacement controller to make the loading plates move away from the cube rock specimen, and then controlling the sleeve lifting mechanism to move upwards, and finally taking out the cube rock specimen; and Step 10, opening the nitrogen bottle, aiming the pipelines connected with the nitrogen bottle at the experimental loading device for a jet cleaning, cleaning the true triaxial rock drilling experimental device, and completing the true triaxial rock drilling experiment.

The application has following beneficial effects.

(1) The application provides three directional stresses, changes the magnitudes of the three principal stresses of the rock specimen independently, and solves the shortcomings that a conventional triaxial experimental device may only experiment under a condition that a second principal stress is always equal to a third principal stress;

(2) the application not only simulates a high temperature and high pressure environment of the formation, but also simulates five pressure states of the bit when drilling into the formation, including a vertical stress, bidirectional horizontal stresses, the liquid column pressure and the pore pressure; therefore, a simulation accuracy is improved and the simulation is closer to real conditions;

(3) an arrangement of the loading plates tightly presses the rock specimen, and avoids the friction and the dislocation between the loading plates; the adjacent loading plates are perpendicular to each other, and the contact mode is that the end face and the front face are staggered; meanwhile, a pressing mode of the double bars on each loading plate avoids the uneven stress and the stress concentration;

(4) the bit drills into the rock from bottom to top, and the detritus are separated from the rock mass by the gravity of the broken detritus; compared with a top-down drilling mode of a conventional experimental device, the detritus are discharged in time, so the influence of the detritus on the experimental process is reduced;

(5) the influence of the multiple bits on the rock breaking mechanism may be studied, and the multiple bits, including the PDC bits and the cone bits, may be used; the threaded connection makes the replacement of the bit simple and convenient, so the application is suitable for the study of the rock breaking mechanism of the multiple bits;

(6) the application may study a relationship among the rotation speed, a drilling depth, the temperature, the pressure and the time under a three directional stress condition, and fills in a gap of a true triaxial simulation experimental device in the field of a rock drillability evaluation at present.

DETAILED DESCRIPTION OF THE EMBODIMENTS

Figure 5:
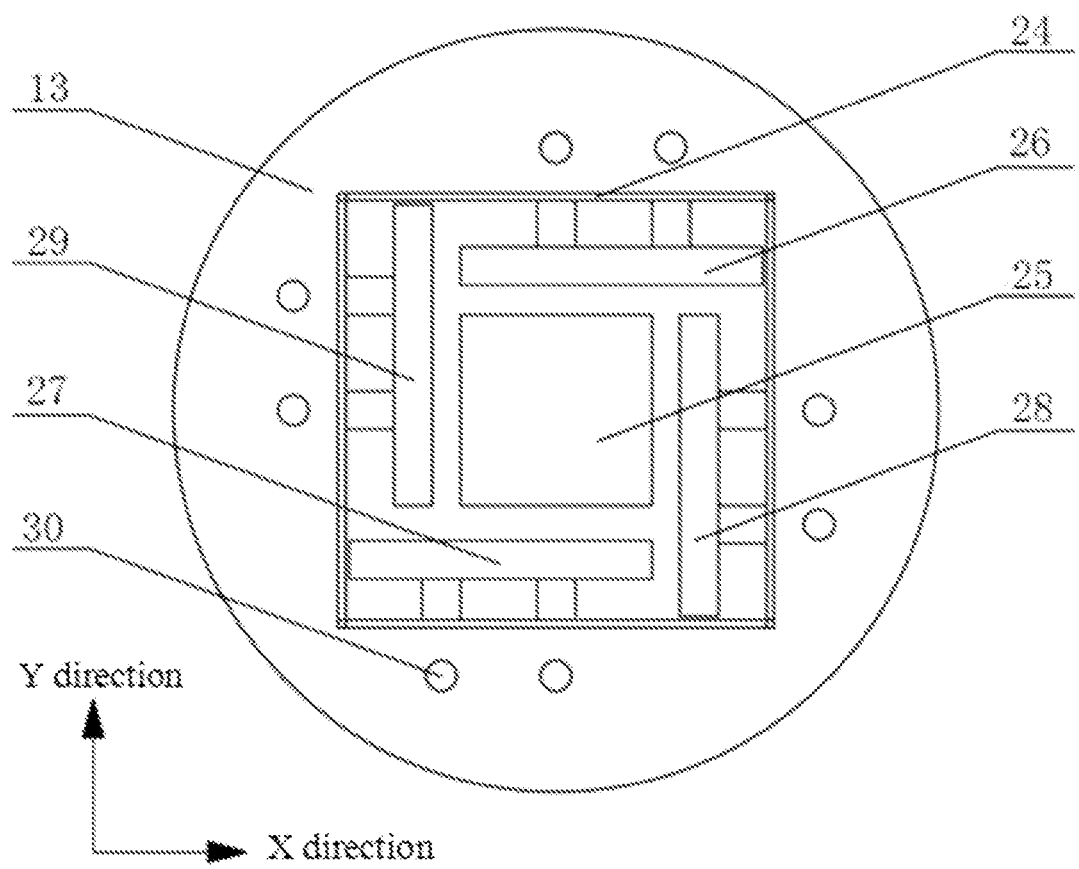
FIG. 5 is a bottom view of a loading chamber and loading plates in an experimental loading module.

In order to better explain the application, the application is further explained below with reference to drawings and specific embodiments. Orientation terms such as "X direction" and "Y direction" are all in a horizontal plane, and an orientation mark in FIG. 5 is used as reference.

Figure 1:
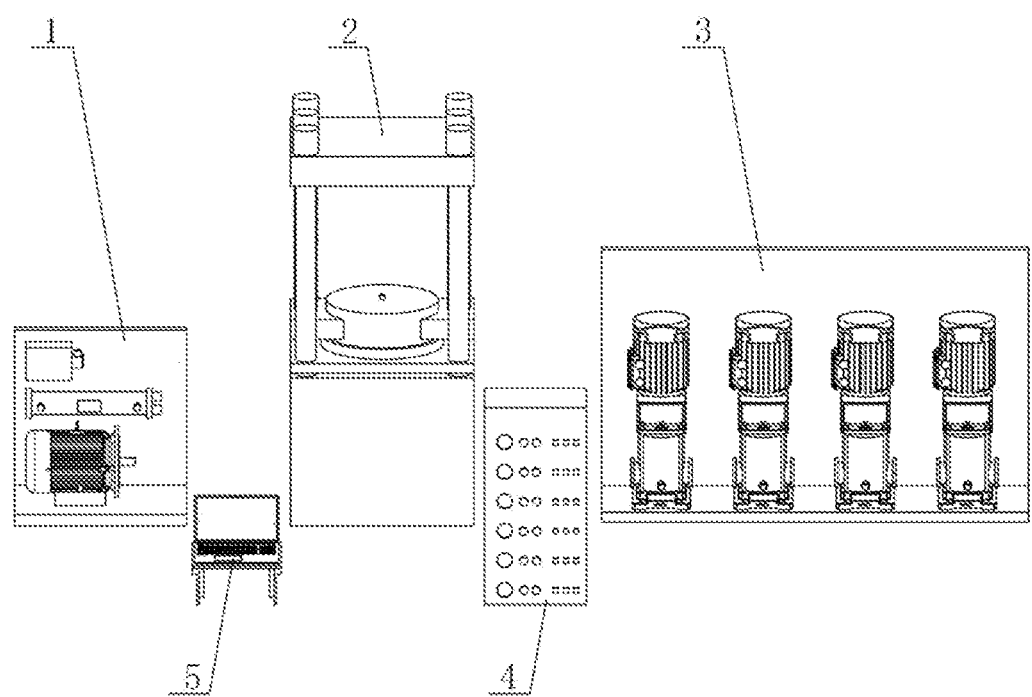
FIG. 1 is a structural schematic diagram of a rock drilling experimental device for simulating the true triaxial conditions of deep well drilling.

The application proposes an embodiment, with reference to FIG. 1; FIG. 1 is a structural schematic diagram of a rock drilling experimental device for simulating true triaxial conditions of deep well drilling proposed by the application.

As shown in FIG. 1, in this embodiment, the rock drilling experimental device for simulating the true triaxial conditions of deep well drilling mainly includes an energy supply module 1, an experimental loading module 2, a hydraulic supply module 3, a parameter control module 4 and a data acquisition module 5.

In this embodiment, the energy supply module 1, the experimental loading module 2 and the hydraulic supply module 3 are connected with each other through pipelines, the parameter control module 4 and the data acquisition module 5 are connected with the experimental loading module 2 through cables, and the parameter control module 4 is provided with controllers.

Figure 2:
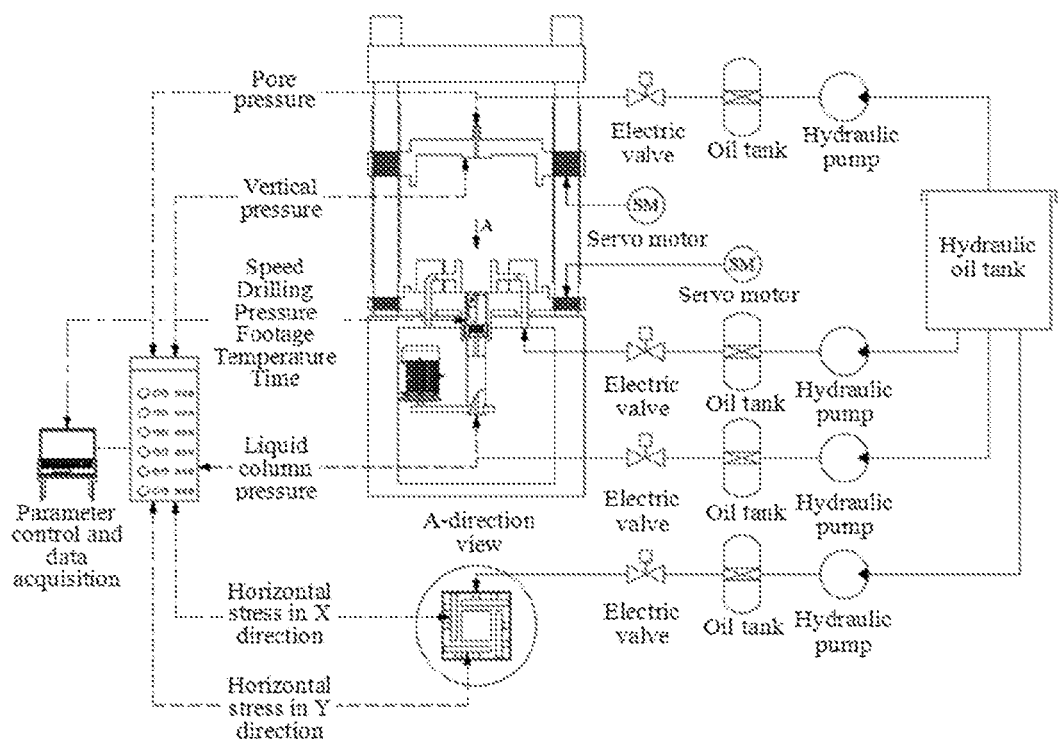
FIG. 2 is a schematic diagram of a principle of a rock drilling experimental device for simulating the true triaxial conditions of deep well drilling.

As shown in FIG. 2, FIG. 2 is a schematic diagram of a principle of a rock drilling experimental device for simulating true triaxial conditions of deep well drilling.

In this embodiment, a hydraulic pump and a servo motor are controlled to work by setting parameters of a temperature, a pressure, a rotation speed and a displacement of the parameter control module 4; the experimental loading module 2 is provided with sensors, which feed back three directional stresses, a liquid column pressure, a pore pressure and the temperature of the experimental loading module 2, and the experimental loading module 2 feeds back signals to the data acquisition module 5 through the cables for data acquisition and output.

Figure 3:
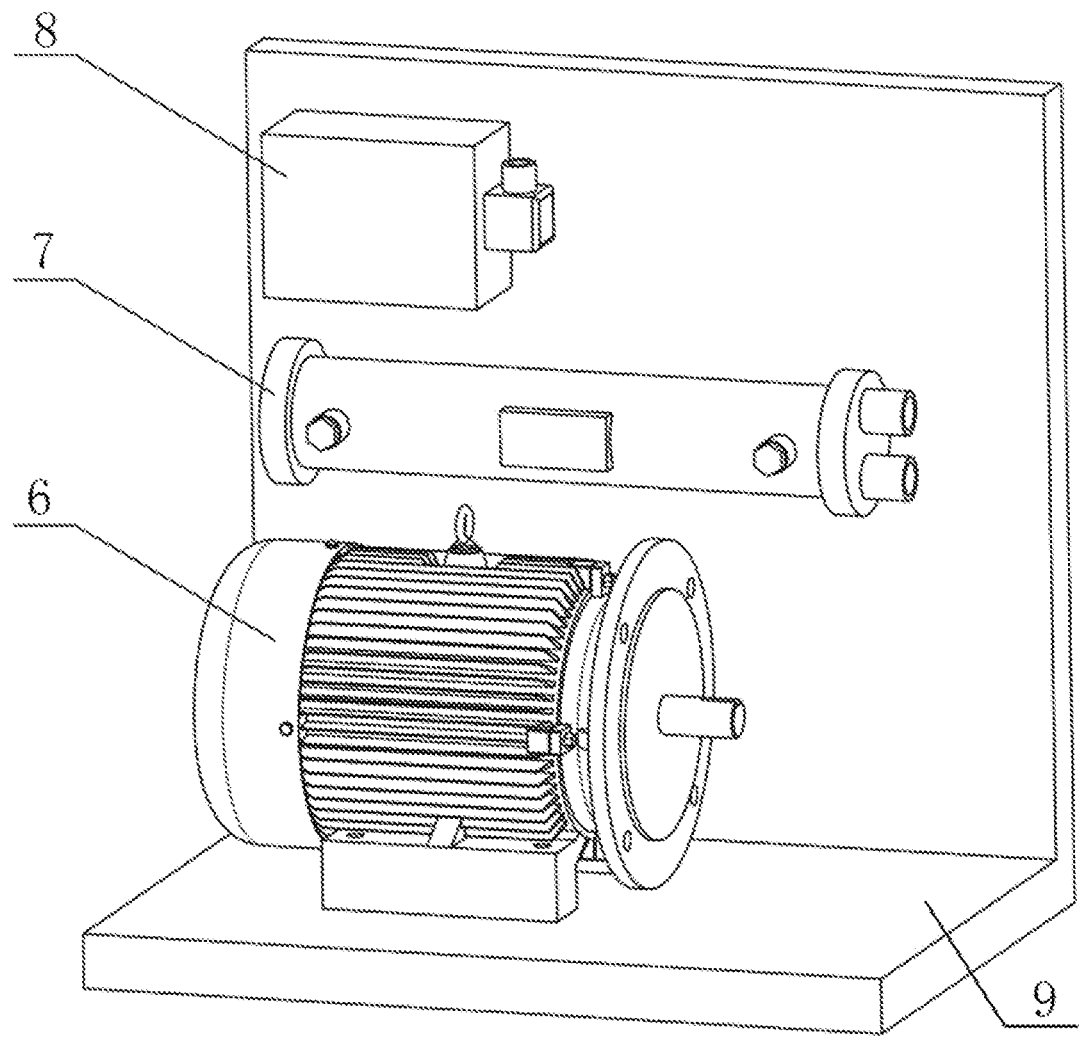
FIG. 3 is an axonometric schematic drawing of an energy supply module.

As shown in FIG. 3, FIG. 3 is an axonometric schematic drawing of the energy supply module.

In this embodiment, the energy supply module 1 includes a three-phase asynchronous motor 6, an oil cooler 7, a differential pressure transmitter 8 and an L-shaped support frame 9; the three-phase asynchronous motor 6 is arranged on a bottom plate of the L-shaped support frame 9; the oil cooler 7 and the differential pressure transmitter 8 are arranged on a side wall of the L-shaped support frame 9; the differential pressure transmitter 8 is arranged above the oil cooler 7; the differential pressure transmitter 8, the oil cooler 7 and the three-phase asynchronous motor 6 are connected in sequence through the pipelines.

Figure 4:
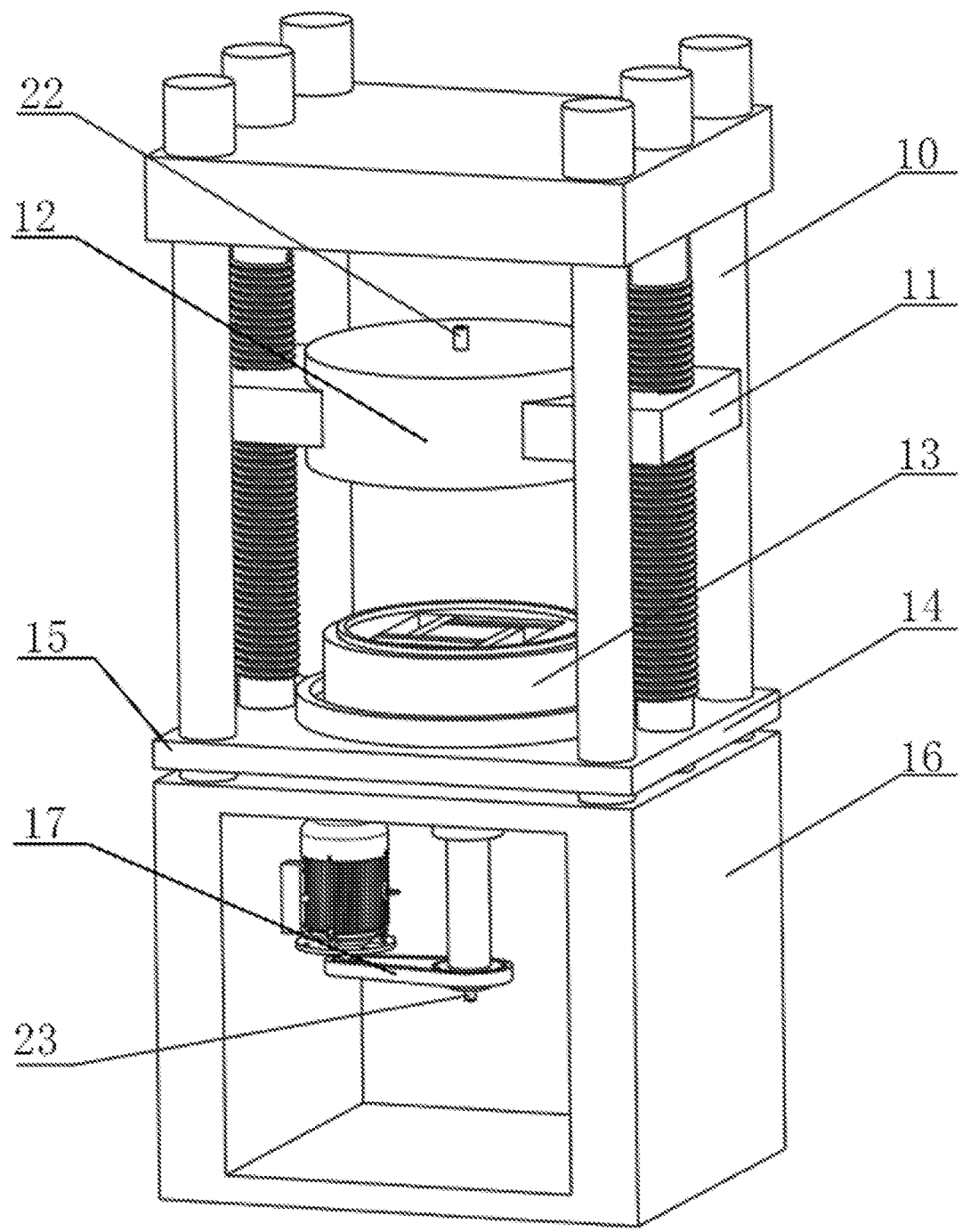
FIG. 4 is an axonometric schematic drawing of an experimental loading module.

As shown in FIG. 4, FIG. 4 is an axonometric schematic drawing of the experimental loading module.

In this embodiment, the experimental loading module 2 includes a column support structure 10, a sleeve lifting mechanism 11, a sleeve 12, a loading chamber 13, a support plate lifting mechanism 14, a support plate 15, a base 16 and a drilling structure 17; the column support structure 10 includes a plurality of smooth columns and threaded columns which are symmetrically arranged on both sides above the base 16; the sleeve 12 is connected with the sleeve lifting mechanism 11; the support plate 15 is connected with the support plate lifting mechanism 14; the sleeve lifting mechanism 11 and the support plate lifting mechanism 14 are connected with the threaded columns on the both sides of the column support structure 10 through threads; the sleeve lifting mechanism 11 is arranged above the support plate lifting mechanism 14; the drilling structure 17 includes a bit 18, a drill rod 19, a transmission chain 20 and a servo motor 21; the bit 18 is matched with the drill rod 19 through a threaded connection; the servo motor 21 is fixedly installed on an inner wall surface of the base 16; one end of the drill rod 19 is connected with the servo motor 21 through the transmission chain 20; and the other end of the drill rod 19 passes through a through hole at the bottom of the support plate lifting mechanism 14 and is installed on a groove.

In an embodiment, a top center of the sleeve 12 is provided with a pore pressure hole 22; a bottom end of the drill rod 19 is provided with a liquid column pressure hole 23.

In a specific embodiment, a design pressure, a design temperature, a minimum wall thickness, a corrosion allowance and material selection requirements are given. According to experimental requirements and current national standards, design parameters of an experimental loading device 102 are given as follows.

When designing the design pressure and the design temperature of the experimental loading module 2, the design pressure of the rock drilling experimental device for simulating the true triaxial conditions of deep well drilling is set to 200 MPa, and a pressure grade of the rock drilling experimental device for simulating the true triaxial conditions of deep well drilling is set to an ultra-high pressure (code U, p≥100.0 MPa), the maximum working pressure is 180 MPa; the design temperature of the rock drilling experimental device for simulating the true triaxial conditions of deep well drilling may be set at 20° C. -200° C.

A test pressure $p_T$ meets a formula:

$$P_T = 1.25 p \frac{[\sigma]}{[\sigma]^t}$$

where:

$P_T$—the test pressure, MPa;

p—the design pressure of the pressure vessel or the maximum allowable working pressure specified on a pressure vessel nameplate, MPa;

$[\sigma]$—an allowable stress of a material at a test temperature, MPa; and $[\sigma]^t$—the allowable stress of the material at the design temperature, MPa.

According to allowable stress values of the following materials at an experimental temperature and the design temperature and the design pressure of the pressure vessel, the test pressure is obtained as follows:

$$P_T = 1.25 p \frac{[\sigma]}{[\sigma]^t} = 1.25 \times 200 \times \frac{230}{230} = 250 (MPa)$$

When designing the corrosion allowance and the minimum thickness of the experimental loading module 2, possible corrosion conditions of the rock drilling experimental device for simulating the true triaxial conditions of deep well drilling are considered, including: a slight acid corrosion caused by a sludge of hydraulic oil, an atmospheric corrosion caused by a long-term exposure to an atmospheric natural environment, and an abrasion corrosion caused by broken rock particles wrapped by the hydraulic oil; when a nominal thickness is within a range of 8.00-15.0, a negative deviation of a material thickness is −0.55 mm; after a shell is processed and formed, the minimum thickness of a low alloy steel container excluding the corrosion allowance is less than 3 mm; after meeting the above conditions, the design thickness should be ≥4.55 mm, and the minimum thickness of a true triaxial rock drilling experimental device after rounding may be 5 mm.

When selecting the material of the experimental loading module 2, considering that the loading chamber 13 of the rock drilling experimental device for simulating the true triaxial conditions of deep well drilling needs to be forged by metal blank, and the rock drilling experimental device for simulating the true triaxial conditions of deep well drilling also needs to bear higher load and have the above-mentioned corrosion resistance, steel number 35CrMo (low alloy steel) is selected; this steel grade has the allowable stress of 230 MPa at the nominal thickness of ≤300 mm and the temperature of 200° C., and has the allowable stress of 230 MPa at the temperature of ≤20° C., and this steel grade may be used normally at the design pressure of 200 MPa.

As shown in FIG. 5, FIG. 5 is a bottom view of the loading chamber and loading plates in the experimental loading module.

In this embodiment, the loading chamber 13 includes a plurality of heating resistors 24, a cube rock specimen 25, a first X-direction loading plate 26, a second X-direction loading plate 27, a first Y-direction loading plate 28, a second Y-direction loading plate 29 and a plurality of horizontal stress holes 30. In an embodiment, the loading chamber 13 has a circular structure; there is a square vacant space in the middle of the loading chamber 13 where the heating resistors 24 are installed, the cube rock specimen 25 is placed, the first X-direction loading plate 26, the second X-direction loading plate 27, the first Y-direction loading plate 28 and the second Y-direction loading plate 29 reciprocate; the heating resistors 24 are uniformly distributed on four circumferential inner walls of the loading chamber 13; two horizontal stress holes 30 are uniformly arranged on each surface of the four circumferential inner walls of the loading chamber 13; the first X-direction loading plate 26, the second X-direction loading plate 27, the first Y-direction loading plate 28 and the second Y-direction loading plate 29 are respectively connected with the loading chamber 13 through the two horizontal stress holes 30 on each surface.

In an embodiment, the first X-direction loading plate 26, the second X-direction loading plate 27, the first Y-direction loading plate 28 and the second Y-direction loading plate 29 respectively face four directions; two adjacent loading plates are perpendicular to each other, and a contact part of the two vertical loading plates is in a staggered contact mode between an end face and a front face; the first X-direction loading plate 26, the second X-direction loading plate 27, the first Y-direction loading plate 28 and the second Y-direction loading plate 29 enclose a structure with a vacant space in the center, and the vacant space is used for placing the cube rock specimen 25. In an embodiment, the hydraulic oil applies a hydraulic pressure to the first X-direction loading plate 26, the second X-direction loading plate 27, the first Y-direction loading plate 28 and the second Y-direction loading plate 29 through eight horizontal stress holes 30, and the first X-direction loading plate 26, the second X-direction loading plate 27, the first Y-direction loading plate 28 and the second Y-direction loading plate 29 slide relative to each other under the hydraulic pressure, so that the loading plates approach to the four horizontal planes of the cube rock specimen 25 until the loading plates completely contact the four planes, and the load is continuously applied to the cube rock specimen 25; the top and bottom of the loading chamber 13 are provided with sealing rings to improve tightness between the loading chamber 13 and the sleeve lifting mechanism 11.

In the specific embodiment, a design wall thickness of the loading chamber 13 needs to be given, and the design parameters of the loading chamber 13 are given according to the experimental requirements as follows:

the formula for calculating the thickness δ of the loading chamber 13 at the design temperature is:

$$\delta = \frac{p_c D_i}{2[\sigma]^t \phi - p_c}$$

where:

$P_c$—a calculated pressure, MPa;
$D_i$—an internal diameter, mm;
$[\sigma]_t$—the allowable stress of the material at the design temperature, MPa;
φ—a coefficient of a welded joint; and
δ—the wall thickness, mm;
the wall thickness δ is obtained as follows:

$$\delta = \frac{200 \times 156}{2 \times 230 \times 1 - 100} = 86.6667 \text{ (mm)}$$

after rounding the wall thickness δ, the wall thickness of the loading chamber 13 is $\delta_1$=90 mm.

Figure 6:
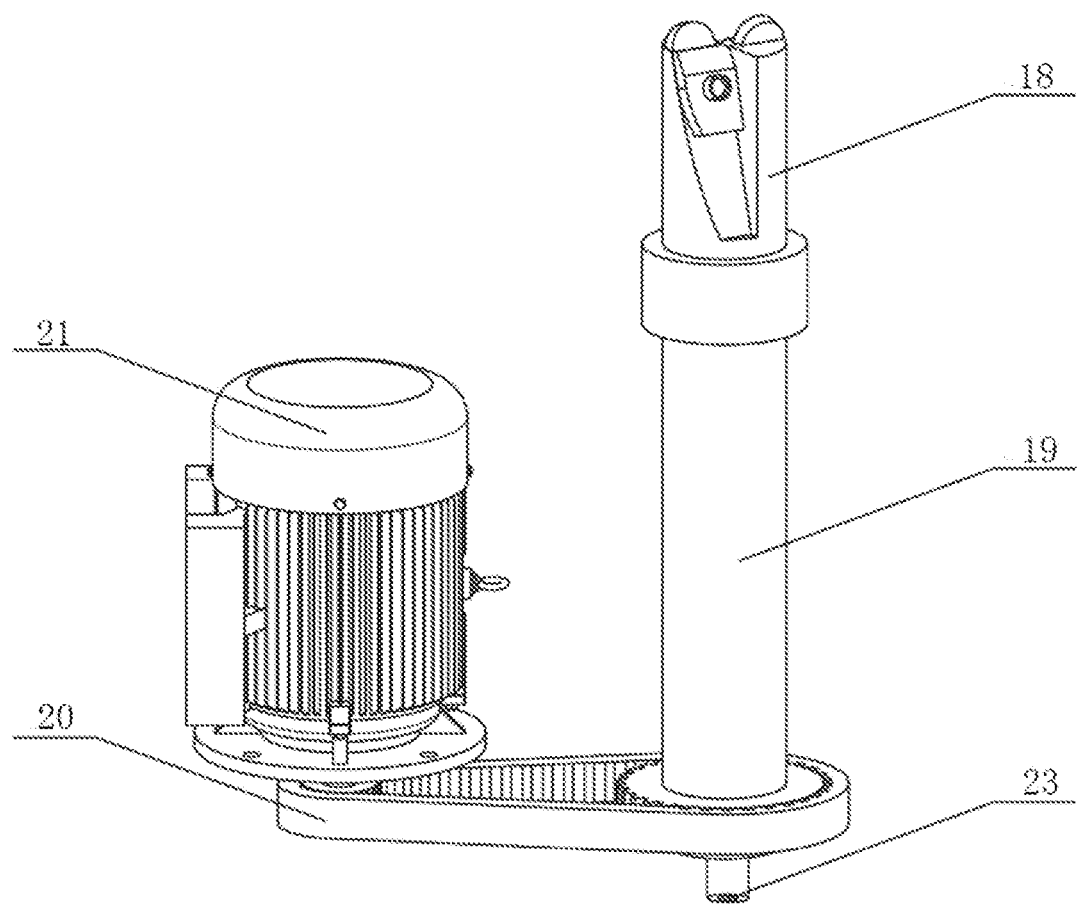
FIG. 6 is a structural diagram of a bit, a drill rod, a transmission chain and a servo motor in an experimental loading module.

As shown in FIG. 6, FIG. 6 is a structural schematic diagram of the bit, the drill rod, the transmission chain and servo motor in the experimental loading module.

In this embodiment, a gear of the servo motor 21 and the gear of the drill rod 19 form a chain transmission through the transmission chain 20, and the drill rod 19 and the bit 18 are matched through a threaded connection; the servo motor 21 is fixedly installed on the base 16, and the servo motor 21 drives the drill rod 19 and the bit 18 to rotate synchronously after being started.

In the specific embodiment, the requirements of the rotation speed need to be given, and the design parameters of the servo motor 21 are given according to the experimental requirements as follows:

a spindle rotation speed is n=55 r/min±1 r/min, and a total efficiency from a motor to a conveyor belt is η=0.96×0.994×0.972×0.99×0.99=0.85, and a required working efficiency $P_d$ of the motor is:

$$P_d = \frac{P_W}{0.96\eta_L}$$

where:
$P_d$—an output power of the motor, Kw;
$P_w$—a total power of a transmission device between the motor and a working machine, Kw; and
$\eta_L$—a product of transmission efficiencies between the motor and conveyor belts at all levels, dimensionless.

Get $P_d$=0.96 kW, take $P_d$=1 kW, and according to a reasonable range of a transmission ratio, take the transmission ratio range of a cylindrical gear transmission first-stage reducer $I_1$=2-5, and V-belt transmission ratio $I_2$=3-4, and then the transmission ratio range is I=$I_1 \times I_2$; and take I=6-20, and then an optional range of a motor speed is:

$$n_d = I \times n = (6 \sim 20) \times 55 = (330 \sim 1100) r/\text{min}$$

where:
$n_d$—a motor speed, r/min;
I—the transmission ratio of rotating components, dimensionless; and
n—the spindle rotation speed, r/min.

Synchronous speeds within a scope are 750 r/min and 1000 r/min, and a selected motor model is YS100L-6, with a rated speed of 960 r/min and a rated power of 1.5 kW.

Figure 7:
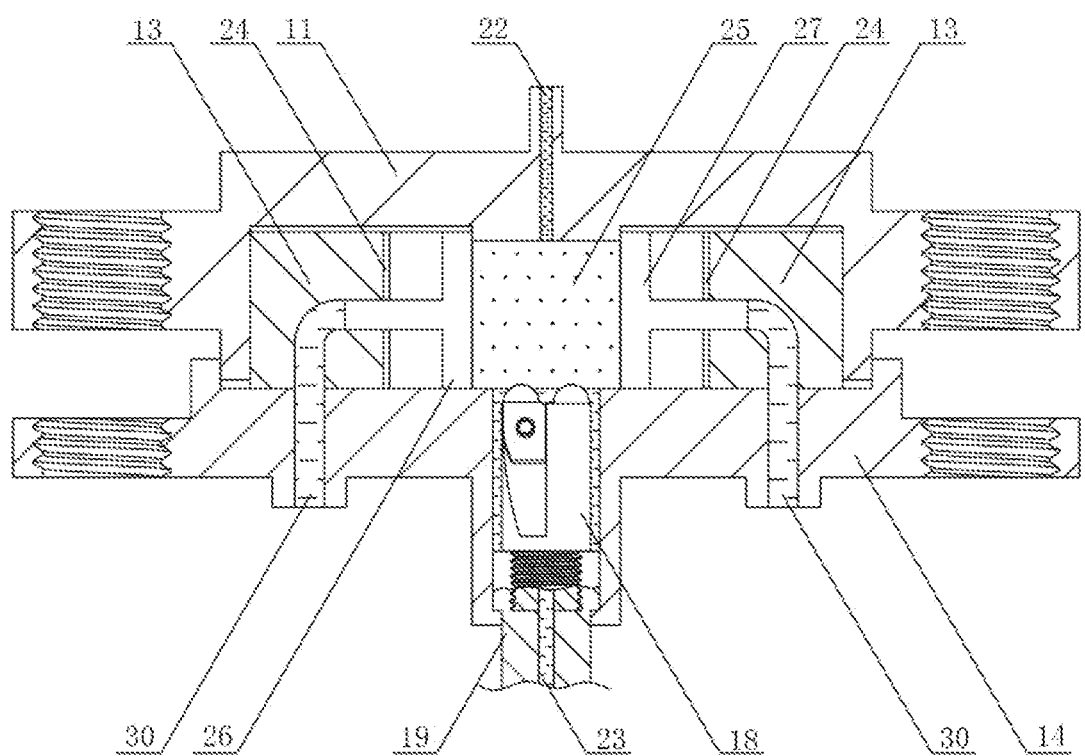
FIG. 7 is a schematic cross-section of an experimental loading module loaded with three directional stresses, a liquid column pressure and a pore pressure.

As shown in FIG. 7, FIG. 7 is a schematic cross-section of the experimental loading module loaded with the three directional stresses, the liquid column pressure and the pore pressure.

In this embodiment, after the sleeve lifting mechanism 11 moves downward in an axial direction to cover the loading chamber 13, the sleeve lifting mechanism 11 continues to move downward in the axial direction to compress the cube rock specimen 25 and continuously applies a vertical stress to the cube rock specimen 25.

At the same time, the hydraulic oil may enter a flow channel through the pore pressure hole 22 at the top of the sleeve lifting mechanism 11 to apply the pore pressure to the cube rock specimen 25; the inner wall of the sleeve lifting mechanism 11 is provided with a sealing ring to improve the tightness between the sleeve lifting mechanism 11 and the loading chamber 13.

Figure 8:
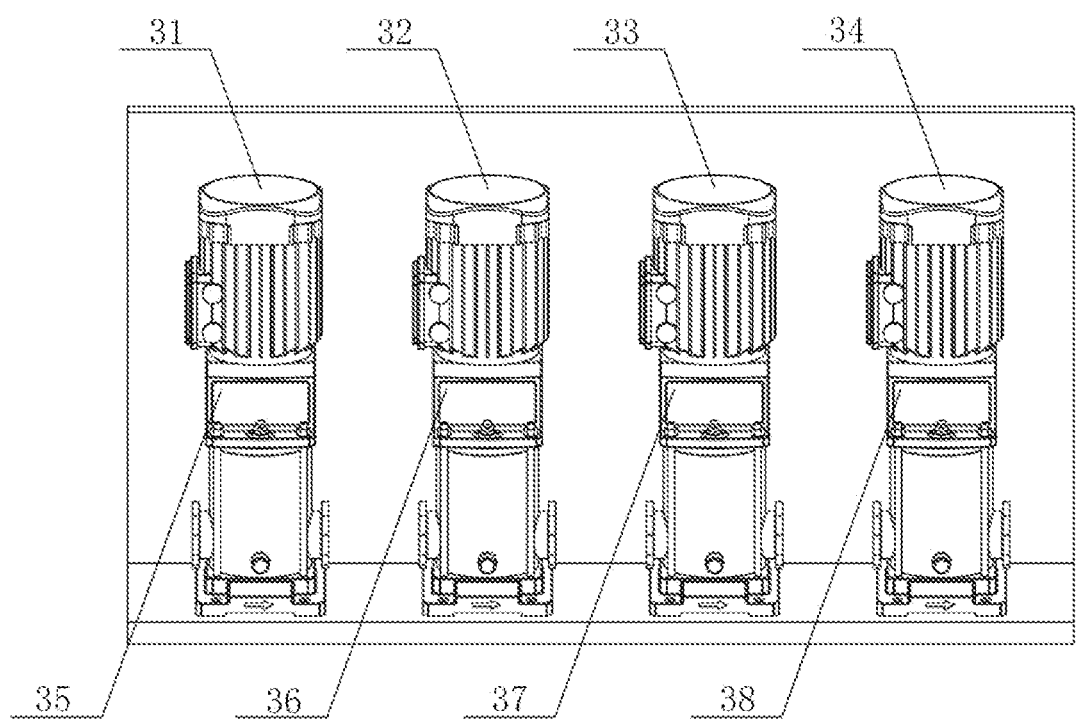
FIG. 8 is a front view of a hydraulic supply module.

As shown in FIG. 8, FIG. 8 is a front view of the hydraulic supply module.

In this embodiment, the hydraulic supply module 3 has four combinations of hydraulic pumps and oil tanks; the hydraulic pumps include a liquid column hydraulic pump 31, a pore hydraulic pump 32, an X-direction hydraulic pump 33 and a Y-direction hydraulic pump 34; the oil tanks include a liquid column pressure tank 35, a pore pressure tank 36, an X-direction pressure tank 37 and a Y-direction pressure tank 38; the hydraulic pumps and the oil tanks are all connected by flanges, and then fixed on the support plate.

An experimental method carried out by the rock drilling experimental device for simulating the true triaxial conditions of deep well drilling includes following steps:

Step 1, preparing the cube rock specimen 25, selecting an experimental bit 18, installing the bit 18 on the drill rod 19 in a threaded connection way, and starting a data acquisition device to collect real-time data;

Step 2, starting the energy supply module 1, providing an energy power for the rock drilling experimental device by using the three-phase asynchronous motor 6, cooling the three-phase asynchronous motor 6 by using the oil cooler 7, and checking whether a differential pressure of the rock drilling experimental device is within a set value by using the differential pressure transmitter 8;

Step 3, placing the cube rock specimen 25 in a square hole at the bottom of the loading chamber 13;

Step 4, starting the parameter control module 4, operating according to a sequence of a coarse adjustment by using a displacement controller and a precise adjustment by using a pressure controller, controlling the four loading plates to slowly move to the cube rock specimen 25 until the four loading plates completely contact the cube rock specimen 25, and applying a load to the set value;

Step 5, slowly lowering the sleeve lifting mechanism 11 by using the displacement controller, and operating according to the sequence of the coarse adjustment by using the displacement sensor and the precise adjustment by using the pressure sensor, ensuring that the bottom of the sleeve lifting mechanism 11 is tightly attached to the cube rock specimen 25; and then turning on the heating resistors 24 by using the temperature controller, preheating the loading plates and the cube rock specimen 25 until the temperature sensor reaches a predetermined value, and keeping the predetermined value for a period of time;

Step 6, controlling the support plate lifting mechanism 14 to move downwards by using the displacement controller, and in this process, providing a rotary force for the bit 18 without starting the rotation speed controller; the same as an adjustment mode in Step 4, operating according to the sequence of the coarse adjustment by using the displacement sensor and the precise adjustment by using the pressure sensor until the top of the bit 18 contacts the bottom of the cube rock specimen 25;

Step 7, starting the pressure controller to inject the hydraulic oil in the liquid column pressure tank 35 into the liquid column pressure hole 23 and the hydraulic oil in the pore pressure tank 36 into the pore pressure hole 22, and then starting the rotation speed controller and the displacement controller to control the bit 18 to drill according to the set value;

Step 8, collecting, outputting and saving the data of the time, the temperature, the pressure, the rotation speed and the drilling depth in an experimental process by using the data acquisition module 5, and finishing a data acquisition and processing of the experiment;

Step 9, firstly, turning off the rotation speed controller to stop the drilling of the bit 18, and then turning off the pressure controller and connecting a nitrogen bottle to the loading chamber 13 through the pipelines; flowing the hydraulic oil from the pore pressure hole 22 back to the pore pressure tank 36 and from the liquid column pressure hole 23 back to the liquid column pressure tank 35, and turning on the displacement controller to make the loading plates move away from the cube rock specimen 25, and then controlling the sleeve lifting mechanism 11 to move upwards, and finally taking out the cube rock specimen 25; and Step 10, opening the nitrogen bottle, aiming the pipelines connected with the nitrogen bottle at the experimental loading device for a jet cleaning, cleaning the true triaxial rock drilling experimental device, and completing the true triaxial rock drilling experiment.

The above embodiments are only used to illustrate a technical scheme of the application, but not to limit it. Although the application has been described in detail with reference to the embodiments, it should be understood by those skilled in the art that any modification or equivalent replacement of the technical scheme of the application is not depart from the spirit and scope of the technical scheme of the application, and should be covered by claims of the application.

What is claimed is:

1. A rock drilling experimental device for simulating true triaxial conditions of deep well drilling, comprising an energy supply module, an experimental loading module, a hydraulic supply module, a parameter control module and a data acquisition module; wherein the energy supply module, the experimental loading module and the hydraulic supply module are connected with each other through pipelines; the parameter control module and the data acquisition module are connected with the experimental loading module through cables; the experimental loading module comprises a column support structure, a sleeve lifting mechanism, a sleeve, a loading chamber, a support plate lifting mechanism, a support plate, a base and a drilling structure; the column support structure comprises a plurality of smooth columns and threaded columns which are symmetrically arranged on both sides above the base; the sleeve is connected with the sleeve lifting mechanism; the support plate is connected with the support plate lifting mechanism; the sleeve lifting mechanism and the support plate lifting mechanism are connected with the threaded columns on both sides of the column support structure through threads; the sleeve lifting mechanism is arranged above the support plate lifting mechanism; the drilling structure comprises a bit, a drill rod, a transmission chain and a servo motor; the bit is matched with the drill rod through a threaded connection; the servo motor is fixedly installed on an inner wall surface of the base; one end of the drill rod is connected with the servo motor through the transmission chain; the other end of the drill rod passes through a through hole at the bottom of the support plate lifting mechanism and is installed on a groove.

2. The rock drilling experimental device for simulating the true triaxial conditions of deep well drilling according to claim 1, wherein the energy supply module comprises a three-phase asynchronous motor, an oil cooler, a differential pressure transmitter and an L-shaped support frame; the three-phase asynchronous motor is arranged on a bottom plate of the L-shaped support frame; the oil cooler and the differential pressure transmitter are arranged on a side wall of the L-shaped support frame; the differential pressure transmitter is arranged above the oil cooler; the differential pressure transmitter, the oil cooler and the three-phase asynchronous motor are connected in sequence through pipelines.

3. The rock drilling experimental device for simulating the true triaxial conditions of deep well drilling according to claim 1, wherein a top centre of the sleeve is provided with a pore pressure hole; a bottom end of the drill rod is provided with a liquid column pressure hole.

4. The rock drilling experimental device for simulating the true triaxial conditions of deep well drilling according to claim 1, wherein the loading chamber comprises a plurality of heating resistors, a cube rock specimen, a first X-direction loading plate, a second X-direction loading plate, a first Y-direction loading plate and a second Y-direction loading plate; and a tail part of each loading plate is uniformly distributed with two stress bars and a plurality of horizontal stress holes.

5. The rock drilling experimental device for simulating the true triaxial conditions of deep well drilling according to claim 4, wherein a top and a bottom of the loading chamber are provided with sealing rings.

6. The rock drilling experimental device for simulating the true triaxial conditions of deep well drilling according to claim 5, wherein the loading chamber has a circular structure; there is a square vacant space in the middle of the loading chamber where the heating resistors are installed, the cube rock specimen is placed, the first X-direction loading plate, the second X-direction loading plate, the first Y-direction loading plate and the second Y-direction loading plate reciprocate; the heating resistors are uniformly distributed on four circumferential inner walls of the loading chamber; two horizontal stress holes are uniformly arranged on each surface of the four circumferential inner walls of the loading chamber; the first X-direction loading plate, the second X-direction loading plate, the first Y-direction loading plate and the second Y-direction loading plate are respectively connected with the loading chamber through the horizontal stress holes on each surface.

7. The rock drilling experimental device for simulating the true triaxial conditions of deep well drilling according to claim 6, wherein the first X-direction loading plate, the second X-direction loading plate, the first Y-direction loading plate and the second Y-direction loading plate respectively face four directions; two adjacent loading plates are perpendicular to each other, and a contact part of the two vertical loading plates is in a staggered contact mode between an end face and a front face; the first X-direction loading plate, the second X-direction loading plate, the first Y-direction loading plate and the second Y-direction loading plate enclose a structure with a vacant space in the centre, and the vacant space is used for placing the cube rock specimen.

8. The rock drilling experimental device for simulating the true triaxial conditions of deep well drilling according to claim 1, wherein the hydraulic supply module has four combinations of hydraulic pumps and oil tanks; the hydraulic pumps comprise a liquid column hydraulic pump, a pore hydraulic pump, an X-direction hydraulic pump and a Y-direction hydraulic pump; the oil tanks comprise a liquid column pressure tank, a pore pressure tank, an X-direction pressure tank and a Y-direction pressure tank; the hydraulic pumps and the oil tanks are all connected by flanges, and then fixed on the support plate.

\* \* \* \* \*